United States Patent [19]

Dolhay et al.

[11] 4,250,892

[45] Feb. 17, 1981

[54] APPARATUS FOR THE REMOVAL OF CONTENTS OF BODY CAVITIES BY SUCTION AND/OR FOR SAMPLING DURING AN OPERATION

[75] Inventors: Balazs Dolhay; Zsolt Barczy, both of Budapest, Hungary

[73] Assignee: Chinoin Gyogyszer es Vegyeszett Termekek Gyara, Budapest, Hungary

[21] Appl. No.: 953,614

[22] Filed: Oct. 23, 1978

[30] Foreign Application Priority Data

Oct. 24, 1977 [HU] Hungary .............................. DO 416

[51] Int. Cl.³ ............................................ A61B 17/22
[52] U.S. Cl. .................................... 128/758; 128/768; 128/276; 128/304
[58] Field of Search ............... 128/304, 276, 760, 763, 128/766, 768, 757, 758

[56] References Cited

U.S. PATENT DOCUMENTS

| | | | |
|---|---|---|---|
| 2,715,899 | 8/1955 | MacLean | 128/304 X |
| 3,506,010 | 4/1970 | Murr | 128/276 |
| 3,542,031 | 11/1970 | Taylor | 128/304 |
| 3,661,144 | 5/1972 | Jensen et al. | 128/304 X |
| 3,670,732 | 6/1972 | Robinson | 128/304 X |
| 3,721,244 | 3/1973 | Elmaleh | 128/304 |
| 3,769,980 | 11/1973 | Karman | 128/304 |
| 3,774,612 | 11/1973 | Marco | 128/304 |
| 3,863,624 | 2/1975 | Gram | 128/304 X |
| 4,036,232 | 7/1977 | Genese | 128/768 X |
| 4,055,167 | 10/1977 | Bernstein | 128/304 X |

Primary Examiner—Kyle L. Howell
Attorney, Agent, or Firm—Karl F. Ross

[57] ABSTRACT

A system for removing materials from a body cavity which comprises a flexible catheter having a rigid end formed with an edge and connected to a filter vessel to which a suction source is also connected together with sources of washing and treating agents for the evacuated body material.

9 Claims, 14 Drawing Figures

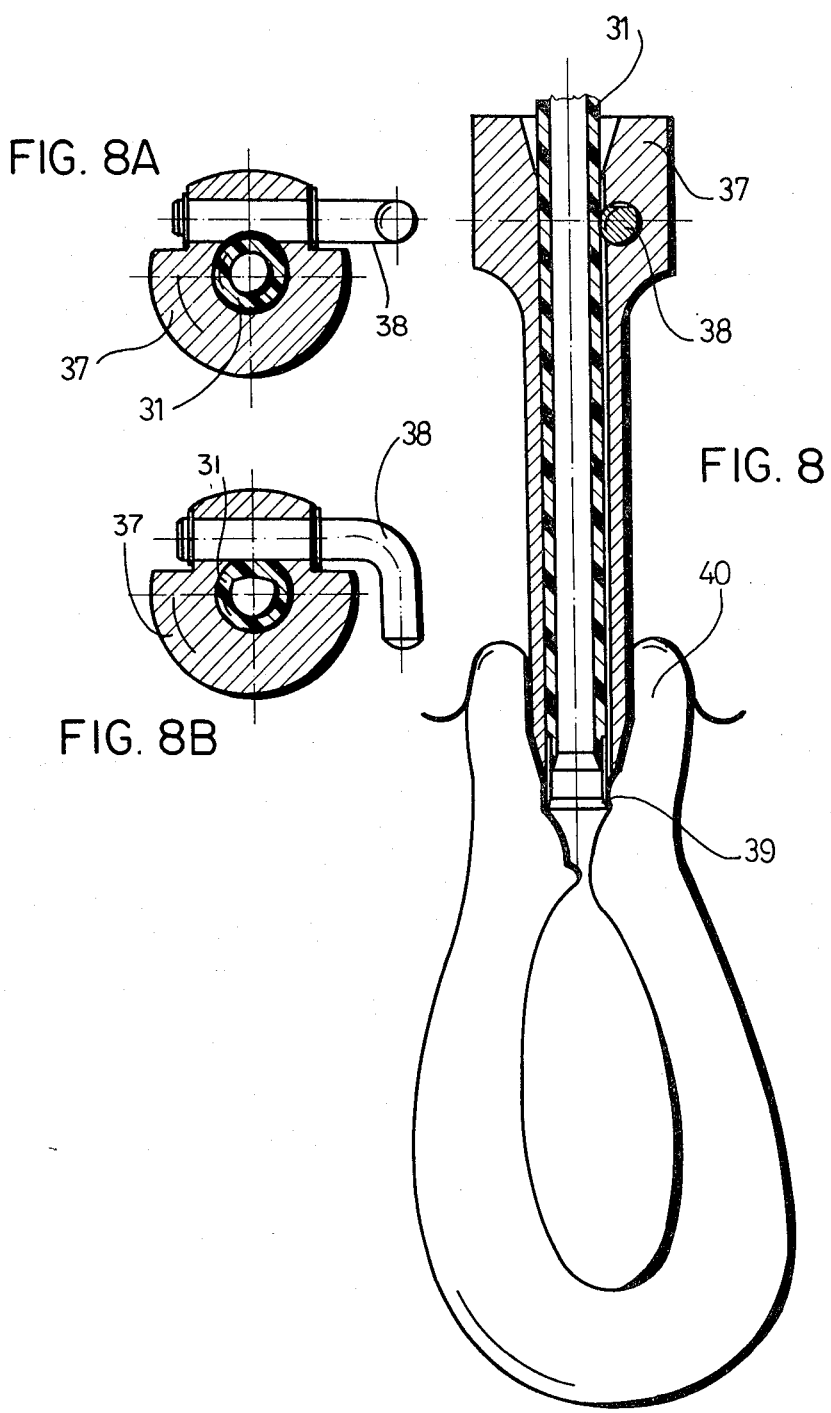

APPARATUS FOR THE REMOVAL OF CONTENTS OF BODY CAVITIES BY SUCTION AND/OR FOR SAMPLING DURING AN OPERATION

FIELD OF THE INVENTION

The invention relates to an apparatus for the removal of contents of body cavities by suction, and/or for sampling during an operation, which has a vacuum unit, a catheter and a container, a filter being provided between the catheter and vacuum unit.

BACKGROUND OF THE INVENTION

Removal of content of body cavities by suction is well known in medical practice. There are several apparatuses known for carrying out operations with a vacuum method. For example the system of English Pat. No. 1,273,387 for gynecological purposes is based on the principle of suction. In essence the catheter is connected with a container provided with a filter, which also serves as the handle of the instrument.

A drawback of this system is that the material drawn from the cavity can not be observed in practice. Owing to the fast rate of coagulation, separation of the tissue parts and clotted blood does not take place in spite of the filtering either. No provision is made either for the fixing and disinfection of the tissue parts, preferably with formalin, which can be necessary for subsequent—e.g. microscopic—examination.

Replacement of the catheter, which is necessary in some cases cannot be carried out or is carried out only with difficulty with the simultaneous removal of the container cover. The device does not permit cytological sample taking with identical instrument.

Another well-known apparatus is described in U.S. Pat. No. 3,721,244. Its drawback in addition to those already mentioned, is that the catheter is not replaceable at all.

Another disadvantage is that the cervix may have to be previously dilated in relation to the diameter of the catheter. This can be a main cause of subsequent gynecological complaints by the patient, especially in case of an injured cervix.

Thus a disadvantage of the instruments known so far is that they do not perfectly separate the material removed from the cavity and necessary for the subsequent examination from the unnecessary other material, e.g. from the blood; direct observation of the materials removed from the cavity is not available or is difficult; further preparation, e.g. fixing of the tissues for instance for subsequent microscopic examination, is not possible. In addition, generally little consideration is given to the necessity of careful treatment of the cervix; replacement of the catheter during operation is not possible or is difficult to achieve; and simultaneous cytological sample taking is not possible in the course of the operation.

We know of no suction system which, besides filtering the biopsy material obtained from the cavity, facilitates by any other means its direct examination with the eye, and enables its immediate preparation for further examination. This is highly significant, especially in gynecological practice, where the careful inspection of the removed endometrium may decisively influence the further course of the operation. The immediate washing of the withdrawn material is necessary for the inspection. The immediate preparation of the material for histological examination significantly increases the reliability of the examination.

Highly significant among the suction catheters are those, which are used for intrauterine gynecological suction catheters. The medical practice has special requirements concerning the gynaecological suction catheters. The end of a suction catheter should be able to pass a catheter through the cervix after minimal dilation and without injury. Injury of the cervix is very frequent, causing premature births, subsequent sterility and cancerous diseases. At the same time, for removal of the more persistently sticking materials an edge should be provided by which the removal of the endometrium persistently adhering to the rear wall of the uterus, can also be ensured. At the same time it is essential that the suction catheter should not cause injury, e.g. perforation of the uterus.

In this respect the above described systems are not satisfactory. The suction catheter according to U.S. Pat. No. 3,721,244 does not have an edge and its passage through the cervix is free, from risk of injury. This is also true in the apparatus of the English Pat. No. 1,273,387, in which the handle of the catheter is the collecting container itself.

Thus it is apparent that the known rigid suction catheters do not solve the mentioned problems. Although an edge can be provided on the instruments made from metal, the rigidity of the catheter frequently leads to injury of the uterus. For this reason flexible suction catheters, such as the flexible catheters of U.S. Pat. No. 3,506,010 have become popular. This arrangement considerably reduces the risk of injury, although the flexible material does not allow a rigid edge to be formed; thus these instruments are not suitable for sample taking, or for the removal of persistently sticking materials.

OBJECT OF THE INVENTION

The principal object of the present invention is to provide a universal apparatus of the class described which is suitable for the immediate washing of materials sucked out of the cavity, for the separation of certain parts and for carrying out certain treatments, preferably fixing.

A further object is to provide an instrument, which permits the removal of persistently sticking material particles, similarly to the method carried out with a curette scoop, and which at the same time precludes excessive dilation of the cavity entrance and reduces the risk of injury.

SUMMARY OF THE INVENTION

According to the invention the container in the apparatus between the catheter and vacuum unit is a washing-treating container, and is connected with a washing-agent source and/or a treating agent source or sources. The number of the washing-agent treating-agent sources is optional.

The washing- and treating agent source can be a liquid container connected by a regulating and locking device to the washing-treating container.

The washing-treating container may consist of a container cover provided with connecting elements and a replaceable vessel provided with a closing means applicable after the vessel has been removed from the cover.

The washing-treating container may be of transparent material at least in part, and advantageously is provided with a bag-like filter insert suitably connected to the cover.

When a flexible catheter is used as part of the apparatus, the catheter has suction openings surrounded with rigid material parts. The suction opening is surrounded by edges at least in part of rigid material.

In flexible plastic suction catheters the material parts surrounding the suction openings can be made rigid by known physical or chemical processes. Surrounding the suction openings with rigid material can be accomplished by making the end of the suction catheter from metal. Alternatively, only the parts surrounding the suction openings are formed as an insert made from metal or another rigid material.

When the suction catheter has a closed distal end, this end part, i.e. the end to be introduced into the cavity, is rounded asymmetrically.

The apparatus according to the invention may be provided with a guide tube having a distal end positioned in the entrance of the cavity and facilitating the penetration of the suction catheter into, and its controlled movement within the cavity. The proximal end of the guide tube is so constructed and arranged that its moving and fixing are simple and safe.

The guide tube may consist of several parts fixed to each other and can be releasably fixed to the suction catheter.

The outer part of the guide tube may be provided with a handle and with position marks referring to the position in relation to the cavity entrance.

In the apparatus of the invention the catheter is not connected directly to the container but rather is joined to the washing-treating container by a suction tube. The use of flexible suction tube is very advantageous because it allows free movement and feeling with the catheter.

The catheter side of the suction tube is provided with a conventional connecting part, whereby the catheter is simply connectible and easily replaceable.

The invention is based partly on the recognition that the visual evaluation of the tissue parts removed during operation is necessary for the further course of the operation. Direction of the further examination of the removed materials too can be decided in the course of the visual evaluation. For this purpose the continuous, immediate removal of the materials, e.g. blood, disturbing judgement, is necessary.

Similarly it is necessary to preserve the structure of the material to be examined, i.e. to begin preparations for examination by fixing the specimen as soon as possible. Removal of material from the cavity generally involves ample bleeding, thus a major part of the withdrawn material is blood, disturbing the examination of the cells and tissue parts, or making it impossible. Thus the extraction of the examination material has been complicated heretofore and therefore it is generally not properly realized in the practice; hence a significant part of the removed material is not available for examination. The main point of the invention is that by the continuous washing and filtering of the materials removed from the cavity by suction, the parts necessary for further examination can be separated in the suction apparatus itself without mechanical damages. These specimens can be visually evaluated and by treatment with some liquid agent they can be prepared for further examination.

A significant advantage of the invention is that it ensures the simultaneous separation of the materials to be examined from other materials within the suction apparatus itself and enables continuous visual evaluation during operation.

By ensuring the possibility of treatment with various liquids, the apparatus is suitable for preparation, fixing, disinfection, dying of the examination material, or for preparation of cytochemical, histochemical, ultramicroscopic, autoradiographic examination, etc. A further advantage is that by ensuring the fastest fixing possible, autolysis of the cell organelles is preventible.

The configuration of the catheter end according to the invention ensures that in the course of its introduction into the cavity, the risk of injury to the cavity entrance is minimal. The guide tube for introducing the catheter into the cavity also reduces the risk of damaging the cavity entrance. In its application excessive dilatation of the cervix is avoidable. Without use of the guide tube the cervix has to be dilated significantly, partly because of the easier manipulation and partly because of the spontaneous contraction during operation. A further advantage is that by using the guide tube, material can be obtained from the cavity of the uterus without the injury of the hymen.

The flexible catheter of the invention considerably reduces injury to the body cavity because of its flexibility; at the same time with the aid of the suction openings fitted with edges, the contents of the cavity, including persistently sticking materials as well, are easily removed.

In many cases, e.g. in gynaecological practice, upon removal of the contents of uterus, it is an important, that no removable material should remain in the cavity. This requirement is met by the catheter according to the invention, by simultaneously ensuring the removal of material with the suction holes provided with cutting edges, and its evacuation by the aid of the suction effect.

Another advantage of the asymmetrically rounded catheter end is significant especially in its gynaecological application.

With this construction, in the course of passing the catheter through the cervix by turning the suction catheter while it is being pushed in, the risk of injuring the inner orifice of the uterus is considerably reduced.

This is because the inner orifice of the uterus is situated asymmetrically in relation to the line of the cervix, thus with the asymmetrically rounded end of the suction catheter, the orifice of the inner uterus can be more readily found and when it is pushed in, the lip of the inner orifice is not in frontal contact with the catheter end.

Application of the asymmetrically rounded catheter end according to the invention includes advantages with other cavity entrances too, since by turning of the catheter its end moves concentrically, thereby considerably facilitating the progress in the cavity entrance.

BRIEF DESCRIPTION OF THE DRAWING

Further details of the invention will become more apparent from the following description taken in conjunction with the accompanying drawing wherein:

FIG. 8 is another guide tube and catheter shown in use and in longitudinal cross sections; and FIGS. 8A and 8B are transverse sections in different operative positions of the assembly of FIG. 8.

SPECIFIC DESCRIPTION

Figure 1:
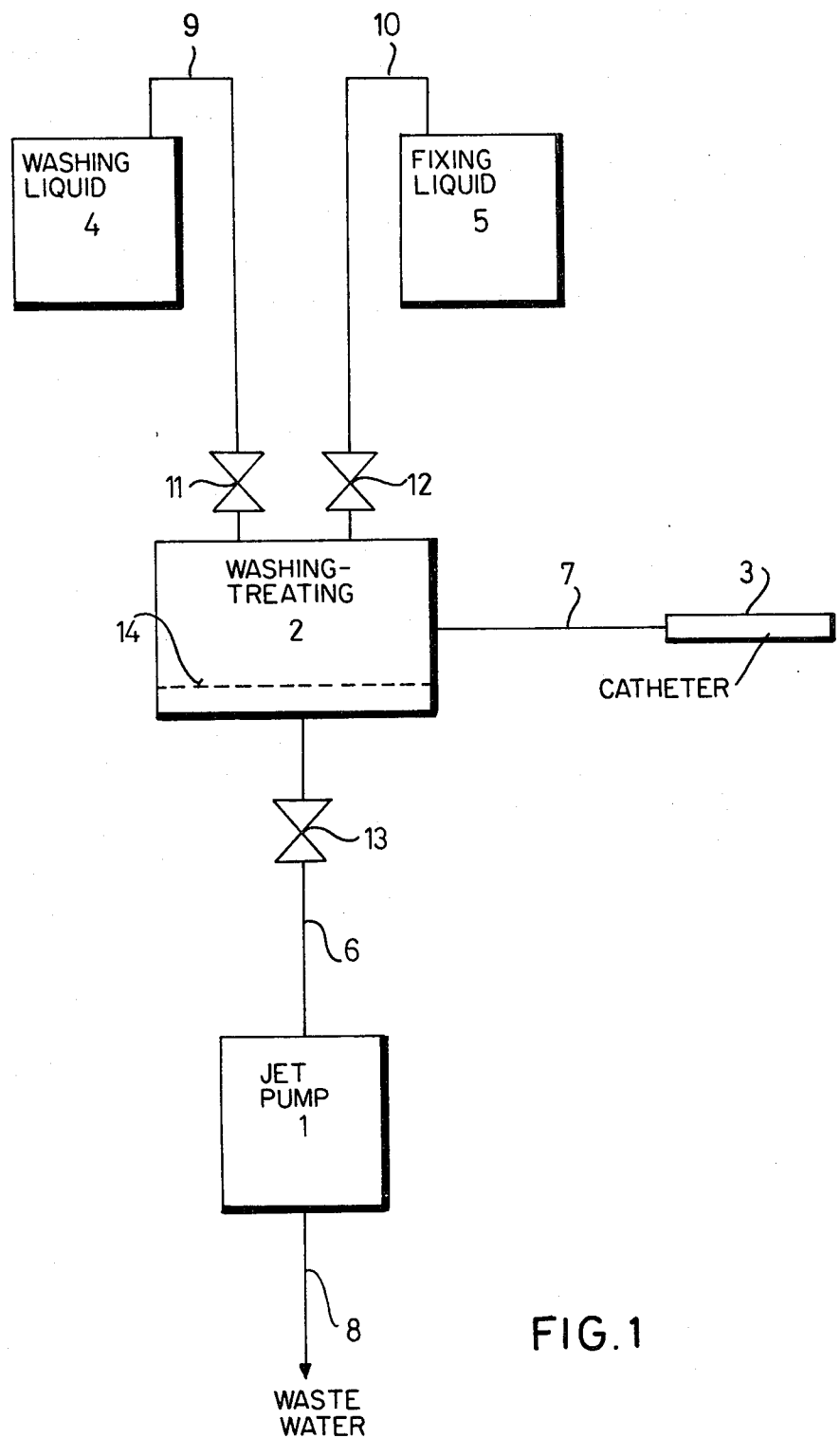
FIG. 1 is a block diagram outlining an apparatus according to the invention.

Referring to FIG. 1, an ejector jet pump 1 with tubing 6 is connected to a washing-treating container 2. This is connected with catheter 3 through suction tube 7. Tubing 8 is used for discharge of the waste water. The washing liquid container 4 is connected to the washing-treating container 2 through tubing 9, and to the fixing liquid container 5 through tubing 10. Tubings 9, 10, and 6 are provided with valves 11, 12, and 13, respectively.

Operation of the apparatus is the following:

Ejector jet pump 1 in the open position of valve 13 creates a vacuum in the washing-treating container 2. As a result of the vacuum, a suction effect develops at the suction openings of catheter 3 and, depending on the position of the valves 11 and 12, washing liquid and fixing liquid flow from containers 4 and 5, respectively, into the washing-treating container 2. The arrangement of containers 4 and 5 is such that their maximum liquid level is lower than the level of the washing-treating container 2. Thus the flow of liquid will occur only in case of a vacuum. Upon introducing the catheter 3 into the uterus, the endometrium is removable, e.g. in the course of interruption of gravidity. The sucked material passes through suction tube 7 into the washing-treating container 2, where the washing liquid washes out the blood, while the tissue particles are captured on the built-in replaceable filter 14, and thus they are held back. The bloody washing water passes continuously through tubing 6, ejector jet pump 1 and tubing 8 into the sewage canal. The quantity and time of applying the washing liquid and fixing liquid may be chosen at the technician's discretion. After completion of the operation, the tissue parts (e.g. those necessary for histological examination) separated from the blood, washed and fixed, are removable from the washing container 2.

Figure 2:
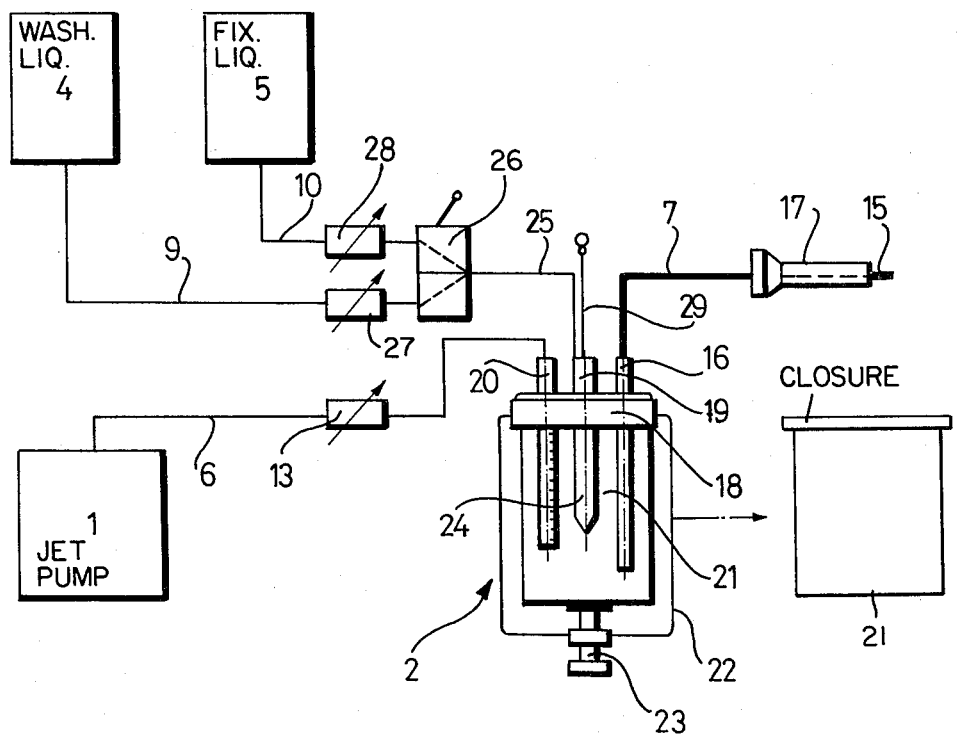
FIG. 2 is a more detailed illustration of the apparatus shown in FIG. 1.

FIG. 2 shows the washing-treating container 2 with the connected units. Catheter 3 connected through suction tube 7 to stub 16 of the washing-treating container 2, can be passed through the hole of guide tube 17 and preferably fixed in it. Cover 18 of the washing-treating container 2 is provided with suspension element in the form of a tube stub 19 supported by element 29. The connecting tube stubs 16, 19 and 20 are carried by cover 18. The transparent vessel 21 and cover 18 are locked airtight with a clamping element 23 of a fixing device 22. Filter insert 24 is on the extension of tube stub 19 reaching into the interior of vessel 21. Tubing 25 is connected to tube stub 19 and runs to the outlet of a selector valve 26. Tubing 9, provided with choke valve 27, is connected to one of the inlets of selector valve 26, the other end of which is connected to the washing liquid container 4. Tubing 10 provided with choke valve 28 and starting from fixing container 5, is connected to the other inlet of selector valve 26. Tubing 6, provided with valve 13, is connected to tube stub 20 leading to the ejector jet pump 1.

Ejector jet pump 1 creates a vacuum in the washing-treating container 2, through tubing 6 in the open position of valve 13. As a result of the vacuum at one of the open positions of the selector valve 26, a quantity of the washing liquid selected by choke valve 27 flows from the washing liquid container 4 through tubing 25 and, in the other open position, a quantity of the fixing liquid selected by choke valve 28 flows from the fixing liquid container 5 into the washing-treating container 2, while at the suction openings of the distal end of catheter 3 a suction effect develops, depending on the positions of valves 13, 27, 28 and 26. Removal of the contents of a cavity takes place with the help of this suction effect in the course of operation with the apparatus as follows.

The distal end of the guide tube 17 is introduced into the cervix. The catheter 3 is then passed through the hole of guide tube 17 for removal of the contents of the uterus. The materials sucked out of the cavity, pass through tube stub 16 into the washing-treating container 2, from which the liquid components (e.g. blood) as a result of the continuous washing are discharged through tube stub 20, while the other components (e.g. tissues) necessary for further examination, remain in vessel 21. This introduction of the washing liquid takes place simultaneously with removal of the contents of the uterus, while application of the fixing liquid may take place at the end of the removal operation, immediately after the washing. The washed and fixed material may be stored in vessel 21 after releasing the clamping element 23. Vessel 21 can be closed with a locking element, such as a stopper.

The suction openings at the end of the suction catheter of the invention to be introduced into the cavity are provided with a knife-like edge. For example the catheter is made from polyethylene tube and its end to be introduced into the cavity is hardened by a chemical process, e.g. by soaking in gasoline, thereby dissolving the softeners. The sharp-edged suction opening settles on the hardened material part.

Figure 4:
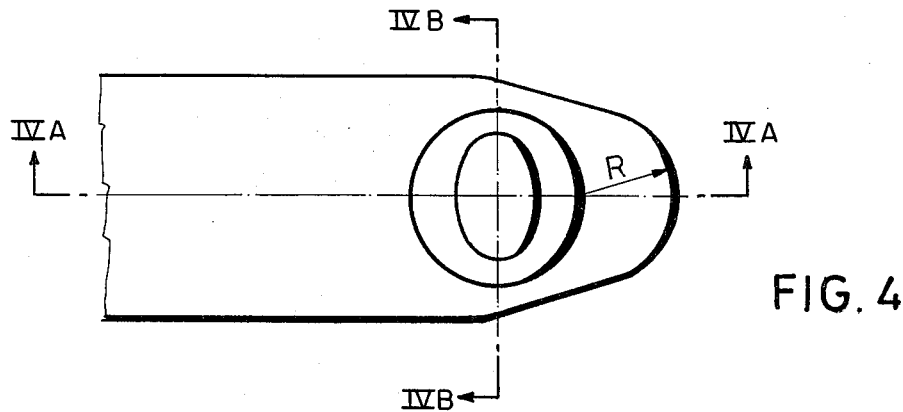
FIG. 4 is another catheter in plan view.
Figure 4A:
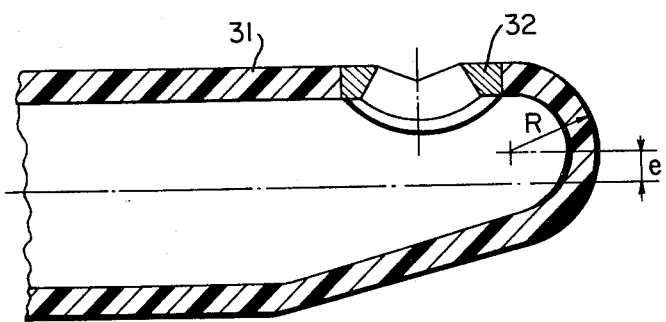
FIGS. 4A and 4B are sections along lines IVA—IVA and IVB—IVB, respectively, of FIG. 4.
Figure 4B:
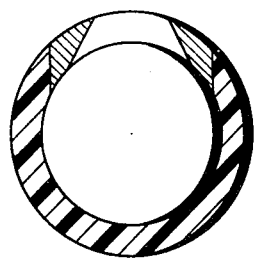

In the embodiment shown in FIG. 4 (see also FIGS. 4A and 4B) a metal insert 32 is placed in the suction opening of the flexible catheter tube 31, at the end of which reaching to the outer mantle of the catheter tube 31, a sharp orifice edge is developed.

Figure 5A:
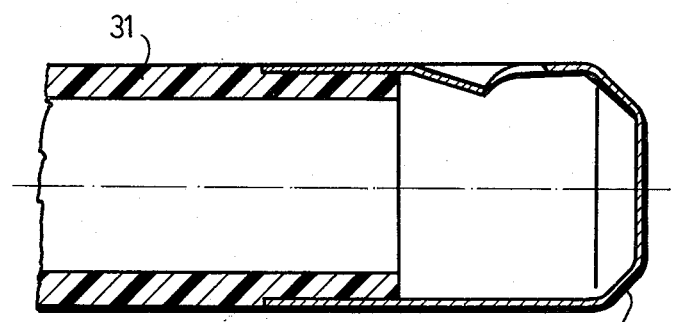
FIG. 5A is a section along line VA—VA of FIG. 5.
Figure 5:
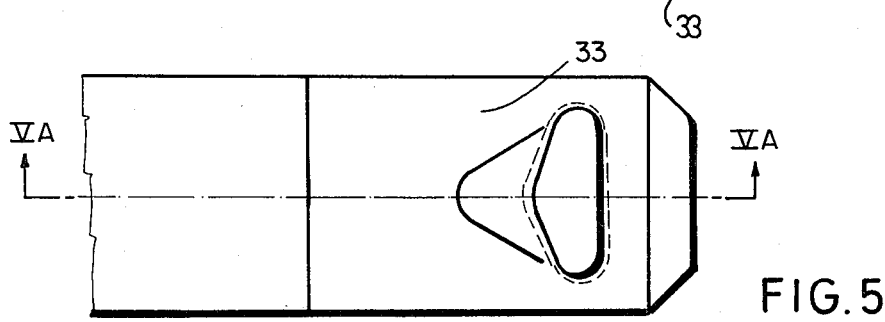
FIG. 5 is still further catheter in plan view.

In the embodiment of FIG. 5, the end of the catheter tube 31 to be introduced into the cavity has a tip 33 made from metal, and the suction opening is formed on this tip.

Figure 6:
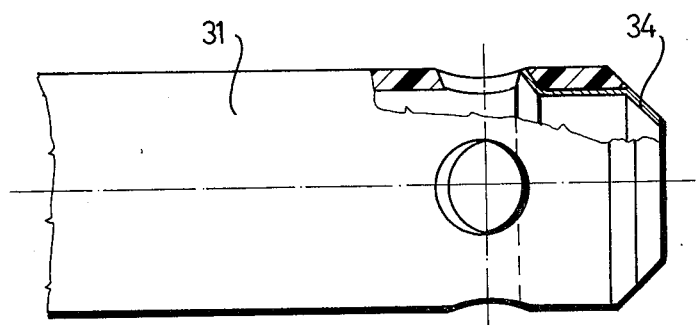
FIG. 6 is again a further catheter in partial section.

FIG. 6 shows a further structural design. Here a metal bush 34 is fixed in the open end of the catheter tube 31. In this embodiment the metal bush 34 and thus the catheter are open in the axial direction.

Figures 3A, 3B:
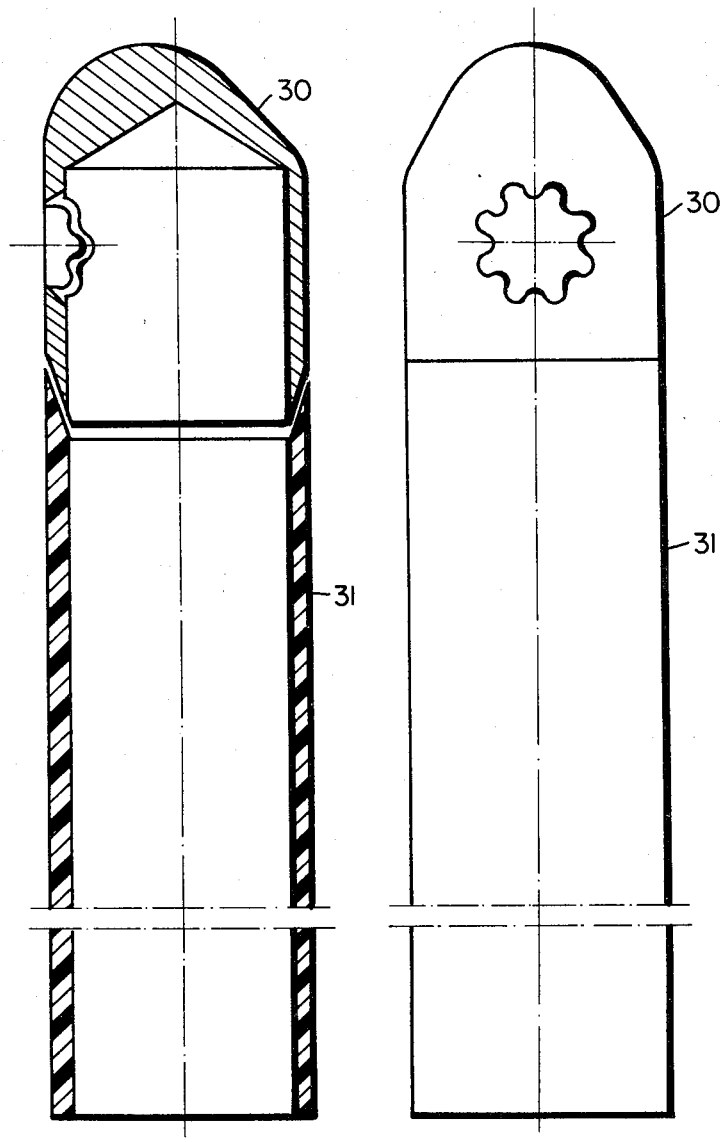
FIGS. 3A and 3B are a plan view of a catheter used in the apparatus according to the invention, and a sectional view thereof, respectively.

The suction catheter is advantageously closed in axial direction and is asymmetrically rounded. The conception of asymmetrical rounding means that centerline of the catheter tube and that of the rounding do not coincide. The enveloping suface of the rounding may be a surface of rotation, e.g. a spherical surface. The asymmetrical rounding can be seen from FIGS. 4, 4A and 4B. Here the catheter tube ends in a sphere of radius R, arranged with eccentricity e. Another example of the asymmetrical rounding is seen in FIGS. 3A and 3B. In this embodiment the metal end 30 is rounded asymmetrically. The shape and size of the hole running in the length of the guide tube 17 suits the shape and size of the suction catheter, i.e. the suction catheter can be easily passed through the hole of the guide tube. The external form at one end of the guide tube suits the shape and size of the cavity entrance, while the axial canal at the other end is preferably tapered, and its external shape may be handle-like. A guide tube serving this function can be seen in FIG. 7. One end of the guide tube 17 fits into the cavity entrance 35. The catheter can then be fed easily into the cavity through the hole of the guide tube 17 in such a way that movement of the suction catheter is not prevented by the spontaneous contraction of the cavity entrance, without the risk of injury. Use of the guide tube is very advantageous in gynaecological practice.

Figure 7:
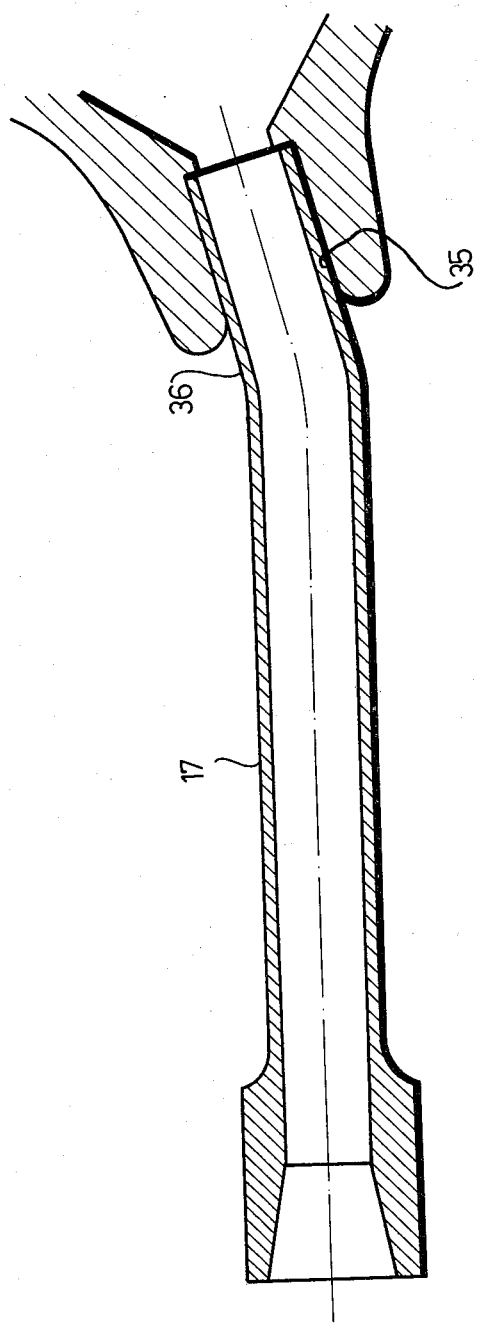
FIG. 7 is the guide tube pertaining to the apparatus, shown in section and as it is used.

The guide tube introduced preferably only up the inner orifice of the uterus, may be straight or slightly bent in respect to its centerline. FIG. 7 shows a bent guide tube. FIG. 8 shows another embodiment of the catheter and guide tube. The lock pin 38 is in the thickened part of guide tube 37. In one position (FIG. 8A) of the lock pin the catheter can be freely moved in the guide tube. By turning the lock pin 38, the catheter tube 31 can be fixed in guide tube 37 (FIG. 8B). The catheter tube 31 is provided with a metal tip 39 at its end to be led into the cavity. This catheter development is especially suitable in gynaecology for taking samples from the cervical canal. FIG. 8 shows such an application. The catheter fixed with lock pin 38 in guide tube 37, in the course of its introduction into the cervix 40, separates valuable examination material from the endoceruix. By a turn of the lock pin 38, catheter tube 31 is releasable and the operation—with or without catheter change can be continued with the same apparatus without interruption. At a preferable embodiment of the guide tube, the visible part of the outer mantle outside the cavity entrance is provided with marks, e.g. notches with numerical symbols—in order to facilitate estimation of the position of the distal end of the guide tube and the inner orifice of the uterus in relation to each other.

What we claim is:

1. An apparatus for the evacuation of the contents of a body cavity which comprises:
    a flexible catheter having at least one end insertable into a body cavity and formed with an opening;
    a container provided with a filter subdividing the interior of the container into a first chamber communicating with another end of said catheter and a second chamber;
    a suction source connected to said second chamber for evacuating said container and drawing material from said body cavity through said catheter into said first chamber and at least in part onto said filter; and
    two sources of liquid connected to said container at said first chamber, said catheter being flexible substantially over its entire length and being formed at said end with a metallic rigid member provided with a lateral opening for communication with the body cavity, said end being rounded axially ahead of said opening in the direction of insertion into the body cavity, said rigid member forming a sharp edge adjacent said lateral opening, a washing-agent source and a fixing-agent source being each connected to said chamber at said first chamber and provided with means for sequential treatment of material on said filter with liquids from these sources.

2. The apparatus defined in claim 1 wherein said wahsing-agent source and said fixing-agent source are respective liquid receptacles connected by respective valves to said container, said suction source being connected by a further valve to said container.

3. The apparatus defined in claim 2 wherein a bag-like filter is attached to said cover and reaches into said vessel.

4. The apparatus defined in claim 2 wherein said container is composed at least in part of transparent material.

5. The apparatus defined in claim 4 wherein said container is at least in part composed of plastic and is disposable after use.

6. The apparatus defined in claim 1 wherein said container comprises a cover affixed to said other end of said catheter, a vessel sealingly engageable with said cover forming said chambers and replaceable in said container, and a closure element applicable to the vessel upon its separation from said cover.

7. The apparatus defined in claim 1 wherein said rigid member is a metal insert in a wall of the flexible catheter.

8. The apparatus defined in claim 1 wherein the rigid member is a metal shell affixed to the flexible material of the catheter.

9. The apparatus defined in claim 1, further comprising a guide tube insertable in the body cavity and adapted to pass said catheter, and means for affixing said guide tube to said catheter.

* * * * *